United States Patent [19]

Klingler et al.

[11] 4,060,618
[45] Nov. 29, 1977

[54] QUATERNARY XANTHINYLALKYL NORTROPINE

[75] Inventors: Karl H. Klingler, Langen; Rudolf Aurich, Karben; Silke Habersang, Maintal, all of Germany

[73] Assignee: Deutsche Gold- und Silber-Scheideanstalt Vormals Roessler, Frankfurt, Germany

[21] Appl. No.: 656,085

[22] Filed: Feb. 6, 1976

[30] Foreign Application Priority Data

Feb. 21, 1975 Austria .................................. 1355/75

[51] Int. Cl.² .................... A61K 31/52; C07D 473/08
[52] U.S. Cl. ...................................... 424/253; 260/256
[58] Field of Search .......................... 260/256; 424/253

[56] References Cited

U.S. PATENT DOCUMENTS 3,472,861  10/1969  Zeile et al. ........................... 260/256
3,505,337  4/1970   Zeile et al. ........................... 260/292

Primary Examiner—Paul M. Coughlan, Jr.
Attorney, Agent, or Firm—Cushman, Darby & Cushman

[57] ABSTRACT

There are prepared quaternary xanthinylalkylnortropine derivatives of the general formula I

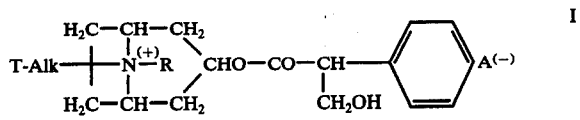

where T represents a theophyllinyl-7 radical or a theobrominyl-(1)-radical, Alk is a straight or branched chain alkylene group having 2 to 10 carbon atoms or such a group substituted by a hydroxyl group, R is an alkyl group of 1 to 4 carbon atoms and $A^{(-)}$ is an equivalent to an anion of a physiologically compatible mono- or polyvalent acid. The compounds are useful as medicines having a spasmolytic activity.

12 Claims, No Drawings

QUATERNARY XANTHINYLALKYL NORTROPINE

The present invention is directed to quaternary xanthinylalkyl nortropine derivatives of general formula I

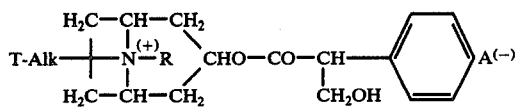

where T represents a theophyllinyl-(7) radical or a theobrominyl-(1) radical, Alk is a straight or branched chain alkylene group having 2 to 10 carbon atoms or such a group substituted by a hydroxyl group, R is an alkyl group of 1 to 4 carbon atoms and $A^{(-)}$ is an equivalent of an anion of a physiologically compatible or pharmacologically acceptable mono- or polyvalent acid.

Thus, Alk can be ethylene, propylene, trimethylene tetramethylene, hexamethylene, octamethylene, decamethylene, 2-methyltrimethylene, 2-hydroxyhexamethylene, or 3-hydroxyhexamethylene, R can be methyl, ethyl, propyl or butyl.

Generally the group Alk consists of 2 to 6 carbon atoms, preferably 2 to 4 carbon atoms. In case the group Alk is substituted by a hydroxyl group, then the hydroxyl group is found only on a carbon atom of the group Alk which is further bound exclusively to carbon and hydrogen. For example, such groups include $-CH_2-CH(OH)-CH_2-$ or $-CH_2-CH(OH)-CH_2-CH_2-$. Preferably, Alk has 3 carbon atoms, i.e., $-(CH_2)_3-$ and $-CH_2-CH(CH_3)-$. For R methyl and ethyl are preferred, methyl being most preferred. T is preferably the theophylline radical.

As anions $A^{(-)}$ there can be used any of the known physiologically compatible and pharmaceutically usable anions of acids. For example, there can be used the anions of sulfuric acid, nitric acid, phosphoric acid, hydrochloric acid, hydrofluoric acid, hydrobromic acid, hydriodic acid or anions of aliphatic saturated or unsaturated fatty acids with 1 to 20 carbon atoms, the anions of phenylcarboxylic acids which in a given case are substituted in the aromatic nucleus by methyl and/or hydroxyl groups, phenalkyl carboxylic acids and naphthalene carboxylic acids, the anions of aliphatic and aromatic sulfonic acids or the anions of camphor sulfonic acids. Preferably there are used the chloride and nitrate.

Individually, for example, as organic acids for the anion $A^{(-)}$ there can be used the following acids: aliphatic monocarboxylic acids, in a given case containing a double bond with 1 to 20 carbon atoms, particularly 1 to 10 carbon atoms, preferably 1 to 6 carbon atoms, such as formic acid, acetic acid, propionic acid, butyric acid, valeric acid, hexanoic acid, decanonic acid, lauric acid, myristic acid, palmitic acid, stearic acid, eicosanoic acid acrylic acid, methacrylic acid, crotonic acid or oleic acid; aliphatic dicarboxylic acids, which, in a given case, contain a double bond, with 13 to 10 carbon atoms, especially 3 to 6 carbon atoms such as malonic acid, fumaric acid, maleic acid, succinic acid, adipic acid, glutaric acid or sebacic acid; aliphatic monohydroxy and dihydroxy monocarboxylic acids with 2 to 6, especially 2 to 3 carbon atoms wherein there are preferably used alpha-monohydroxy carboxylic acids such as lactic acid, glyceric acid or glycolic acid, aliphatic monohydroxy and dihydroxy di and tricarboxylic acids with 3 to 8 carbon atoms, particularly 3 to 6 carbon atoms such as tartronic acid, malic acid, tartaric acid or citric acid; oxocarboxylic acids with 2 to 6 carbon atoms, particularly 2 to 3 carbon atoms, such as glyoxylic acid, pyruvic acid, acetoacetic acid or mesoxalic acid; aromatic carboxylic acid, especially phenyl carboxylic acids or naphthalene carboxylic acids which can also be substituted by hydroxyl groups and/or methyl group and wherein between the carboxyl groups and the aromatic nucleus in a given case there can also be an alkylene bridge with 1 to 3 carbon atoms, which bridge in a given case contains a double bond, and wherein two phenyl or naphthalene radicals can be joined together through a methylene group, such as benzoic acid, toluic acid, cinnamic acid, atropic acid, hydratropic acid, salicyllic acid, hydroxycinnamic acid, paomic acid, naphthoic acid, alpha-naphthalene carboxylic acid; aliphatic sulfonic acids with 1 to 6 carbon atoms, particularly 1 to 3 carbon atoms such as methanesulfonic acid, ethanesulfonic acid, propanesulfonic acid, hexanesulfonic acid; aromatic sulfonic acids, especially benzene sulfonic a acids and naphthalene sulfonic acids which in a given case are substituted by a methyl group such as benzene sulfonic acid, alpha-naphthalene sulfonic acid, beta-naphthalene sulfonic acid, p-toluene sulfonic acid, m-toluene sulfonic acid, o-toluene sulfonic acid, camphor sulfonic acid and halocamphor sulfonic acids (e.g., bromocamphorsulfonic acid).

The compounds of the invention have pharmacodynamical or pharmacological therapeutic activity. Above all, they have an excellent spasmolytic activity, particularly a bronchospasmolytic activity. In comparison to the known agent atropine or other known quaternary atropine derivatives the undesired side effects of the known anticholinergic materials (for example arresting of saliva flow of the saliva secretion by pilocarpine; mydriatic activity) are significantly reduced, for example, with the compounds of the invention.

The compounds of the invention can be produced by reacting a. a compound of the formula $$Z'-Y \qquad \text{II}$$

with a compound of the formula

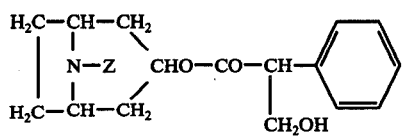

wherein either Z' is the group T—Alk and Z is the group R or Z' is the group R and Z the group T—Alk and Y is a halogen atom, e.g., chlorine, bromine, iodine or fluorine, an aryl sulfonic acid radical $ArSO_2O-$, e.g., from benzene sulfonic acid or p-toluenesulfonic acid, or the radical $ROSO_2$ and in the compounds obtained in a given case the anion $A^{(-)}$ is converted by reaction with an acid derivative into another of the stated anions or b. a compound of the formula

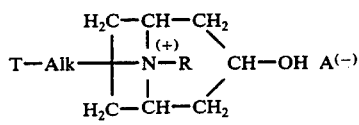

is reacted with a compound of the formula

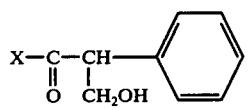

wherein X is a hydroxy group or a halogen atom, e.g., chlorine, bromine, fluorine and wherein the free hydroxy group of formula V can contain a customary protective group (e.g., an ester group; e.g., the acetate group), and in a given case in the compound obtained the anion $A^{(-)}$ can be converted into another anion by reaction with an acid that it is derived from a different anion or the salt of such acid, or c. a compound of formula I wherein the radical T, Alk and R have the stated significance and $A^{(-)}$ is a bromide, iodide, or hydroxy anion is treated with an acid which is derived from a different anion $A^{(-)}$ or a metal salt of such an acid and wherein as acids there can be used those set forth above.

Process (a) is generally carried out in a solvent or suspension agent such as a ketone (e.g., acetone or methylethyl ketone), an alcohol, for example, lower aliphatic alcohols such as methanol, ethanol, propanol and isopropanol, an organic nitro compound such as nitromethane or nitrobenzene, or in other customary agents such as dioxane, acetonitrile, etc., at a temperature between 0° and 150° C., preferably 30° to 80° C. As halogen atoms there can generally be used chlorine, bromine or iodine, especially bromine or iodine. The reaction time in the process can vary between several hours and several weeks. Frequently it is advantageous to produce the compound of formula II freshly beforehand. This is particularly in Hal of formula II is an iodine atom. In such cases the compound of formula II, for example, without previous isolation can be added directly in the reaction liquid in which it occurs. In using compounds of formula II wherein Z′ is the radical R, it is recommended to work in a closed system in case the compounds of formula II is very low boiling.

In compounds of formula II wherein Y represents the radical $ArSO_2O—$, Ar signifies an aromatic radical as, for example, phenyl or naphthyl, in a given case, with one or more lower alkyl radicals (e.g., methyl, ethyl, propyl or butyl (preferably methyl). For example, there can be used p-toluenesulfonic acid alkyl-T esters.

Process (b) is carried out with or without solvent at temperatures between 20° and 150° C., particularly between 40° and 120° C. As solvent or diluent there can be used, for example, benzene, toluene, chlorobenzene or dioxane. Frequently it is favorable to work in a vacuum.

Preferably a compound of formula V is used wherein X is chlorine or bromine.

The compound of formula IV represents a quaternary compound and is employed in the form of a customary salt. Generally it is employed as halide, for example, the chloride, bromide or iodide.

The free hydroxy group of the compound of formula V is suitably protected by a customary protective group. This is particularly true if X is a halogen atom.

For these protective groups there are used for example easily solvolytically splittable acyl groups, which are derived particularly from lower aliphatic acids, e.g., acetic acid or propionic acid. The subsequent splitting off of this group takes place either by simply standing in water or by saponification by means of dilute acids, e.g., hydrochloric acid or sulfuric acid, or by means of basic materials such as potash (potassium hydroxide), soda (sodium hydroxide), aqueous alkali solutions, alcoholic alkali solutions, or ammonia (e.g., aqueous ammonia) at room temperature or at higher temperatures up to 80° C.

The exchange of an anion $A(—)$ (in the products of formula I is carried out in a solvent or suspension medium such as aliphatic alcohols, e.g., methyl alcohol, ethyl alcohol or isopropyl alcohol, water, aliphatic ketones (e.g., acetone) at temperatures between) 0° and 100° C. It is reacted with the acids that supply the desired anion $A^{(-)}$ or with the metal salts of these acids. As metal salts there can be used, for example, silver salts, mercury salts, or even alkali salts, e.g., sodium and potassium salts. In place of the free acids, there can also be used ion exchange resins which are prepared with the corresponding anions $A^{(-)}$ (see *Houben-Weyl Methoden der organischen Chemie*, Vol. I/1, page 521, Vol. II, page 880).

The compounds of the invention are generally obtained as racemates. However, they can also be present as stereoisomers or optically active forms. Diastereoisomer mixtures which happen to occur, for example, can be separated in customary ways, particularly by recrystallization. Optically active products are obtained either by using active starting materials or by resolution of the racemate using the salts of optically active acid as, for example, tartaric acid, dibenzoyl tartaric acid, camphor sulfonic acid. Particularly favorable properties are possessed for example by the levorotatory compounds which are derived from hyoscyamine.

Depending on the process of production, varying amounts of N-isomer compounds can occur (Isomerisin on the nitrogen of the tropine ring system; equatorially and axial configuration). The compounds of the invention can also be present as mixtures of these N-isomeric compounds or even predominantly or entirely in one of the two forms.

Generally there is preferably formed the equatorial form if the theophyllinylalkyl or theobrominylalkyl radical is introduced last, while the axial form, for example, is preferably formed if the smaller radical (for example, methyl group or ethyl group) is last built into the tropine ring system.

The starting compounds used in processes (a), (b) and (c) so far as they are not known can be obtained, for example, in the following manner:

Process (a)

Compounds of formula III wherein Z is the group T—Alk can be obtained for example in the following manner.

By reaction of compounds of the formula

T—Alk—NH₂        VI with succinaldehyde and acetone dicarboxylic acid according to the Robinson-Schöpf-Process described in *Arneimittelforschung*, Vol. 12, pages 305–309 (1962), compounds of the formula

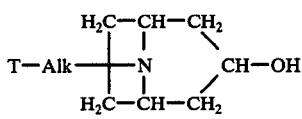
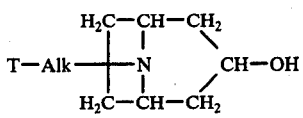

are obtained. The thus obtained compounds are esterified according to the process set forth in *Wolffenstein Chemische Berichte*, Vol. 41, pages 723 to 732 (1908) with an acyl tropic acid halide, particularly the acetyl tropic acid chloride or bromide (temperature about 50° to 100° C.), whereby in a given case the process is operated in a vacuum. The first intermediate product obtained of the formula

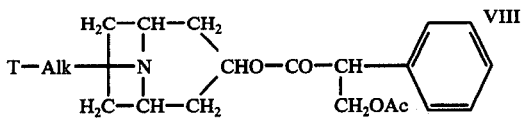

generally need not be isolated but is saponified, for example, in dilute aqueous acid solution at a temperature below 80° C. to compounds of formula III where Z = T—Alk.

In a given case, a compound of formula VII can also be transesterified with the methyl ester of a α-formylphenylacetic acid and, subsequently, the formyl group reduced to the hydroxymethyl group.

The starting materials of formula VI are known.

They are produced from halogenalkyl xanthines and ammonia according to Klingler German Auslegeschrift No. 1,011,424. The chloroalkyl and bromoalkyl xanthines are produced either in customary manner from the hydroxy compounds and $SOCl_2$, $PBr_3$ or $SOBr_2$ or there is reacted potassium theophylline or potassium theobromine (or the corresponding sodium theophylline or sodium theobromine) with a large excess (2 to 10 fold amounts) with a large excess (2 to 10 fold amounts) of a dibromo-alkane or bromo-chloroalkane (e.g., 1-chloro-3-bromopropane) in a lower alcohol (e.g., isopropyl alcohol) at elevated temperature (30° to 150° C.). The process for example is described in example 1 of Klingler German Offenlegungsschrift No. 2,253,075 and related Klingler U.S. Pat. No. 3,896,119. The entire disclosure of the Klingler U.S. patent is hereby incorporated by reference and relied upon.

Compounds of the formula $Z'OSO_2R$ can, for example, be obtained from the alcohols Z"OH and corresponding acrylsulfonyl chlorides. Iodoalkyl compounds of formula II can be obtained from the known chloro or bromo compounds also by reaction with NaI in an inert solvent.

Process (b)

The starting compounds of formula V can be obtained for example, in an analogous manner to the process given in *Chemische Berichte* Vol. 41, page 727 et seq.

The starting compounds of formula IV can be obtained for example in the following manner: By reaction of compounds of formula VI (T—Alk—$NH_2$) with succinaldehyde and acetone dicarboxylic acids in accordance with the Robinson-Schöpf process described in *Arzneimittelforschung*, Vol. 12, pages 305 to 309 (1962) there are obtained compounds of the formula A thus obtained compound is then, for example, quaternarized in customary manner by RHal (Hal = halogen, e.g., chlorine, bromine or iodine) in a solvent or suspension medium at temperatures between 0° and 150° C., and, in a given case, as already described the anion can be exchanged, if desired.

Unless otherwise indicated all parts and percentages are by weight.

EXAMPLE 1

N-[3-theophyllinyl-(7)-propyl]-atropinium iodide 91.3 grams atropine and 164.0 grams of 7-[3-iodopropyl]-theophylline were dissolved in 1 liter of acetonitrile. This solution is heated for 70 hours at 60° C., after cooling to about 40° C. filtered with suction, washed with acetone and dried at 60° C. There are obtained 182.2 grams of iodide.

This compound was also obtained by reacting 192.5 grams of 7-(3-chloropropyl)-theophylline with 112.4 grams of sodium iodide by boiling for seven hours in 4.2 liters of methyl ethyl ketone, filtering and directly heating the thus obtained mixture with addition of atropine for a further 70 hours at 60° C.

The 7-(3-iodopropyl)-theophylline obtained as an intermediate can also be first isolated from the reaction solution and then reacted in the manner given above. For this purpose the filtrate after washing with hot methyl ethyl ketone is concentrated to a small volume. Upon cooling the 7-(3-iodopropyl)-theophylline crystallizes out, is filtered off with suction and is dried in a vacuum. M.P. 135° to 138° C., Yield 237 grams.

EXAMPLE 2

N-[3-theophyllinyl-(7)-propyl]-atropinium chloride

Silver chloride freshly precipitated from 60 grams of silver nitrate with hydrochloric acid was suspended in 350 ml of distilled water and there were introduced at 50° to 60° C. with good stirring 150 grams of N-[3-theophyllinyl-(7)-propyl]-atropinium iodide within 1 hour. Stirring was continued for a further hour without heating, filtered and evaporated in a vacuum. The residue was treated with ethanol, which was subsequently distilled to remove residual water. Then there were added thereto 750 ml of acetone and heating carried out at reflux for 2 hours. The N-[3-theophyllinyl-(7)-propyl]-atropinium chloride was filtered off with suction and dried at 60° C.

Yield: 121.7 grams; M.P.: 220° to 221° C.

EXAMPLE 3

N-[4-theophyllinyl-(7)-butyl]-atropinium bromide

A solution of 2.89 grams of atropine and 4.7 grams of 7-(4-bromo-butyl)-theophyline in 40 ml of acetonitrile were boiled at reflux for 8 days. After cooling it was filtered with suction, washed with acetone and the residue on the filter recrystallized twice from ethanol.

Yield: 2.4 grams; M.P.: 213° to 215° C.

EXAMPLE 4

N-[3-theobrominyl-(1)-propyl]-atropinium iodide

A solution of 2.9 grams of atropine and 5.2 grams of 1-(3-iodopropyl)-theobromine in 40 ml of acetonitrile were heated for 70 hours at 63° C. It was filtered with suction while still warm, stirred up with chloroform, subsequently crystallized from water and finally crystallized from wet methanol.

Yield: 2.5 grams; M.P.: 246° to 248° C.

EXAMPLE 5

N-[3-theophyllinyl-(7)-2-hydroxypropyl]-atropinium iodide

A solution of 2.9 grams of atropine and 5.3 grams of 7-(2-hydroxy-3-iodopropyl)-theophylline in 40 ml of acetonitrile were heated for 120 hours at 60° C. After cooling it was filtered with suction, the filter residue stirred up with chloroform and then recrystallized from wet methanol.

Yield: 2.8 grams; M.P.: 243° to 245° C.

EXAMPLE 6

L-N-[3-theophyllinyl-(7)-propyl]-hyoscyaminium iodide 91.3 grams of L-hyoscyamine and 164.0 grams of 7-(3-iodopropyl)-theophylline were dissolved in a liter of acetonitrile. This solution was heated for 70 hours at 60° C., filtered with suction after cooling to about 40° C., washed with acetone and dried at 60° C. It was recrystallized from methanol plus a little water.

Yield: 77.5%; M.P.: 254°–255° C.

EXAMPLE 7

N-[3-theophyllinyl-(7)-2-methyl-propyl]-atropinium iodide

A solution of 2.9 grams of atropine and 5.4 grams of 7-(3-iodo-2-methyl-propyl)-theophylline in 40 ml of acetonitrile was heated for 70 hours at 63° C. While still warm suction filtering was carried out, stirred up with chloroform, and subsequently recrystallized from wet ethanol.

Yield: 2.1 grams; M.P.: 241°–243° C.

EXAMPLE 8

N-[2-theobrominyl-(1)-ethyl]-atropinium iodide

A solution of 2.9 grams of atropine and 5.0 grams of 1-(2-iodoethyl)-theobromine in 40 ml of acetonitrile were heated for 70 hours at 63° C. While still warm filtering was carried out with suction, the product stirred up with chloroform and subsequently recrystallized from wet ethanol.

Yield: 2.4 grams; M.P.: 185°–188° C.

EXAMPLE 9

N-[3-theophyllinyl-(7)-propyl]-atropinium nitrate

273 Grams of N-[3-theophyllinyl-(7)-propyl]-atropinium chloride were dissolved in 1 liter of distilled water and there were added to this solution at 50°–60° C. a solution of 84 grams of silver nitrate in 0.5 liter of water. Stirring was carried for 1 hour more at 50° C., the mixture evaporated in a vacuum, the residue boiled with ethanol, cooled and the pure nitrate filtered with suction.

Yield: 246 grams; M.P.: 238°–239° C.

EXAMPLE 10

L-N-[3-theophyllinyl-(7)-propyl]-hyoscyaminium chloride

Silver chloride obtained by fresh precipitation of 60 grams of silver nitrate with hydrochloric acid was suspen-ed in 350 ml of distilled water and there were introduced at 50° to 60° C. under good stirring 150 grams of L-N-[3-theophyllinyl-(7)-propyl]-hyoscyaminium iodide within 1 hour. Stirring was continued for a further hour without heating, filtered and evaporated to dryness in a vacuum. Subsequently boiling was carried out while stirring with acetone for 20 minutes and the the L-N-[3-theophyllinyl-(7)-propyl]-hyoscyaminium chloride filtered off with suction and dried at 60° C.

Yield: 120 grams; M.P.: 226°–228° C.

$[\alpha]_D^{20}$ (2% in $H_2O$): $-14.3°$.

EXAMPLE 11

N-[3-theophyllinyl-(7)-propyl]-atropinium-p-toluenesulfonate 9.5 Grams of p-toluenesulfonic acid were dissolved in 50 ml of distilled water and there were added hereto under stirring 6.88 grams of silver carbonate. Heating was carried out with stirring until everything dissolved. Upon cooling, the silver p-toluenesulfonate crystallized out and was filtered off with suction and dried. There were obtained 10.2 grams of silver salt.

3.25 Grams of the thus produced silver salt were dissolved in 75 ml of water and added to a solution of 6.38 grams of N-[3-theophyllinyl-(7)-propyl]-atropinium chloride in 25–30 ml of water. The precipitated silver chloride was filtered off, the filtrate evaporated in a vacuum, the residue boiled with methyl ethyl ketone and filtered off with suction after cooling. After drying at 35° C. there were obtained 6.4 grams of the above-named p-toluenesulfonate. M.P. ∼ 120° C.

EXAMPLE 12

L-N-[3-theophyllinyl-(7)-propyl]-hyoscyaminium nitrate

273 Grams of L-N-[3-theophyllinyl-(7)-propyl]-hyoscyaminium iodide were dissolved in 1 liter of distilled water at 50°–60° C. a solution of 84 grams of silver nitrate in 0.5 liter of water. Stirring was continued for a further hour at 50° C., and the solution filtered and concentrated. Then upon cooling the nitrate crystallized out and it was boiled several times with methanol.

Yield: 230 grams; M.P.: 242°–244° C.

$[\alpha]_D^{20}$ (2% in $H_2O$): $-14.8°$.

The compounds of the invention are suitable for the production of pharmaceutical compositions and preparations. The pharmaceutical compositions as medicines contain as active material one or more of the compounds of the invention, in a given case in admixture with other pharmacologically or pharmaceutically effective materials.

The production of the medicine can take place with the use of known and customary pharmaceutical assistants, carriers and diluents.

Such carriers and assistants include for example those recommended in the following literature as adjuvants for pharmacy, cosmetic and related fields such as in Ullmann's Encyklopadie der technischer Chemie, Vol. 4 (1953), pages 1 to 39, Journal of Pharmaceutical Sciences, Vol. 52 (1963, pages 918 et seq.; H. V. Czetsch- Lindenwald, Hilfstoffe fur Pharmazie und angrenzende Gebiete; Pharm. Ind. Vol. 2 (1961), pages 72 et seq.; Dr. H. P. Fiedler, Lexicon der Hilfstoffe fur Pharmazie, Kosmetik und angrenzende Gebiete, Cantor Kg. Aulendorf i. Wurtt, 1971.

Examples of such materials include gelatin, natural sugars such as sucrose, or lactose, lecithin, pectin, starch (for example, corn starch), tylose (methyl cellulose), talc, lycopodium, silica (for example, colloidal silica), glucose, cellulose, cellulose derivatives, for example, cellulose ethers, in which the cellulose hydroxyl groups are partially etherified with lower aliphatic alcohols and/or lower saturated oxyalcohols, (for example, methyl hydroxypropyl cellulose, methyl cellulose, hydroxyethyl cellulose, stearates, e.g., methylstearate, and glyceryl stearate, magnesium and calcium salts of fatty acids with 12 to 22 carbon atoms, especially saturated acids (for example, calcium stearate, calcium laurate, magnesium oleates, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod liver oil, mono-, di- and triglycerides of saturated fatty acids ($C_{12}H_{24}O_2$ to $C_{18}H_{36}O_2$ and their mixtures, e.g., glyceryl monostearate, glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with mono- (1-to 20 carbon atoms alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ehtylene glycol stearate; such esters of polyvalent alcohols can, in a given case, also be etherified, benzyl benzoate, dioxolane, glycerine formal, glycol furfural, polyglycol ethers with $C_1$-$C_{12}$ alcohols, dimethyl acetamide, lactamide, lactates, e.g., ethyl lactate, ethyl carbonate, silicones (especially middle viscosity dimethyl polysiloxane) magnesium carbonate and the like.

In the production of the preparations there can be used known and conventional solvent aids or emulsifiers. As solvent aids and emulsifiers there can be used, for example, polyvinyl pyrrolidone, sorbitan fatty acid esters such as sorbitan trioleate, lecithin, gum acacin, gum tragacanth, polyethylene oxide condensation products of fatty alcohols, e.g., stearyl alcohol, alkyl phenols or fatty acids, polyoxyethylated fats, e.g., polyoxethylated oleo triglyceride, linolized oleotriglyceride.

Polyoxyethylated means that the materials in question contain polyoxyethylene chains whose degree of polymerization is generally between 2 and 40 and especially between 10 and 20. Such materials can be obtained for example by reaction of hydroxyl group containing compounds (for example, mono- or diglycerides or unsaturated compounds as, for example, such containing the oleic acid radical with ethylene oxide (for example 40 moles of ethylene oxide per mole of glyceride). Examples of oleotriglycerides are olive oil, peanut oil, castor oil, sesame oil, cottonseed oil, corn oil (see also Dr. H. P. Fiedler, "Lexikon der Hilfsstoffe fur Pharmazie, Kosmetik und angrenzende Gebiete", 1971, pages 191 to 195.

Furthermore, there can be added preservatives, stabilizers, buffers, for example, calcium hydrogen phosphate, colloidal aluminum hydroxide, taste correctives, antioxidants and complex formers (for example ethylendiamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value.

As antioxidants there can be used for example sodium meta bisulfite, ascorbic acid, gallic acid; alkyl gallates, e.g., methyl gallate and ethyl gallate, butyl hydroxyanisole, nordihydroguaiaretic acid, tocopherols such as tocopherol and synergists (materials which bind heavy metals by complex formation, for example, lecithin, ascorbic acid, phosphoric acid). The addition of synergists increases considerably the ant-oxidant activity of tocopherol. As preservatives there can be used for example sorbic acid, p-hydroxybenzoic acid esters (for example lower alkyl esters such as methyl ester and the ethyl ester benzoic acid), benzoic acid, sodium benzoate, trichloroisobutyl alcohol, phenol, cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for example, by means of a colloid mill or ball mill), wherein the operation is generally carried out at temperatures between 20° and 80° C., preferably 20° to 50° C.

The medicine can be used for example orally, parenterally and as aerosols.

It is also possible to add further medicinally active material, for example, bronchospasmolytics of a different effective type.

The compounds of the invention by the method of Konzett and Rössler (Arch. exp. Path. Pharmakol., 195, 71 (1940) show a good bronchospasmolytic activity. For example, in the above-mentioned test method at a dosage of 0.5 mcg/kg body weight intravenously on narcolized dogs there is obtained a 50% bronchospasmolysis in relation to an acetylcholine spasm. (1 mcg = 1 microgram ($1\gamma$) = $10^{-6}$ gram).

This bronchospasmolytic activity is comparable with the activity of the known medicine atropine sulfate.

The lowest effective dosage in the above-mentioned animal experiments, for example, is 6.25 mcg/kg intraduodenally, 0.25 mcg/kg intravenously and 0.125% as an aerosol. As a general dosage range for this activity (animal experiments as above) there can be employed for example 6.25–200 mcg/kg intraduodenally, particularly 12.5–20 mcg/kg; 0.25–4 mcg/kg intravenously; particularly 0.5–1 mcg/kg; 0.125–5% as an aerosol, particularly 1%.

The compounds of the invention can be used in treating bronchial asthma, chronic asthmoid bronchitis of various causes, illnesses of the lungs or bronchia with asthma like dyspnoia.

The pharmaceutical preparations generally contain between 0.001 and 20 mg of the active combination of compounds of the invention although this can be varied.

The medicine containing the compounds can be dispensed in the form of tablets, capsules, dragees, dusts, aerosols, or in liquid form. As liquid forms there can be used, for example, aqueous solutions. The preferred forms of use are tablets which contain between 0.1 and 20 mg or solutions which contain between 0.001 and 1% of the active material.

The individual dosages of the active combination of the invention can be for example:

a. between 0.1 to 20 mg in orally administered medicines,
b. between 0.001 and 0.05 mg in parenterally administered medicine (for example, intravenously or intramuscularly),
c. between 20 and 320 mg in medicines for inhalation (solutions or aerosols).

These doses are always based on the free base.

The acute toxicity of the compounds of the invention in the mouse (expressed by the LD 50 mg/kg; method of S. T. Litchfield and F. Wilcoxon; Journ. Pharmacol. Vol. 96 (1949) pages 99, et seq.) on intravenous application is between 14 and 17 mg/kg.

The medicine can be used in human medicine alone or in combination with other pharmacologically active materials.

The process of making the novel compounds can comprise, consist essentially of, or consist of the steps set forth employing the stated materials.

As a further advantage the compounds of the invention cause lower constipation than normally substances with atropine-activity do. Such constipation is a very undesired side effect. For example the spasmolytic activity on the isolated small intestine of the guinea pig against the acetylcholine spasm with the compounds of the invention is significantly lower than with atropine, which means the inventive compounds cause lower constipation.

What is claimed is:

1. A quaternary xanthinylalkyl nortropine derivative of the formula

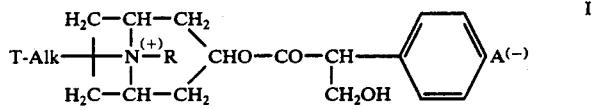

where T is a theophyllinyl-(7) group or a theobrominyl-(1) group, Alk is alkylene group with 2 to 10 carbon atoms or mono-hydroxy-alkylene group with 2 to 10 carbon atoms, the hydroxy group being attached to a carbon atom which is further bound exclusively to carbon and hydrogen, R is alkyl group of 1 to 4 carbon atoms and $A^{(-)}$ is an equivalent of an anion of a pharmaceutically acceptable acid.

2. A compound according to claim 1 where R is methyl.

3. A compound according to claim 2 wherein Alk has three carbon atoms.

4. A compound according to claim 3 wherein Alk has a hydroxy group attached to the middle carbon.

5. A compound according to claim 3 where Alk is alkylene.

6. A compound according to claim 5 wherein T is the theophyllinyl-(7) group.

7. A compound according to claim 6 wherein A is the anion of hydrochloric acid, hydrobromic acid, hydroiodic acid, nitric acid or p-toluenesulfonic acid.

8. A compound according to claim 2 wherein T is theophyllinyl-(7).

9. A compound according to claim 2 wherein A is the anion of hydrochloric acid, hydrobromic acid, hydroiodic acid, nitric acid or p-toluenesulfonic acid.

10. A product according to claim 2 wherein Alk has 2 to 4 carbon atoms.

11. A composition comprising the compound of claim 1 together with a pharmaceutically acceptable carrier, said compound being present in an amount sufficient to provide a spasmolytic effect.

12. A process comprising administering to a mammal a spasmolytically effective amount of the compound of claim 1.

* * * * *